(12) United States Patent
Takeoka et al.

(10) Patent No.: US 8,871,252 B2
(45) Date of Patent: Oct. 28, 2014

(54) PH-RESPONSIVE LIPOSOME

(75) Inventors: Shinji Takeoka, Tokyo (JP); Yousuke Obata, Chiba (JP); Satoru Nakagawa, Toyama (JP); Shinya Ohtsubo, Choufu (JP); Yuji Kawasaki, Motosu (JP)

(73) Assignee: Nanotheta Co, Ltd., Tokyo (JP)

( * ) Notice: Subject to any disclaimer, the term of this patent is extended or adjusted under 35 U.S.C. 154(b) by 466 days.

(21) Appl. No.: 13/255,231

(22) PCT Filed: Mar. 10, 2010

(86) PCT No.: PCT/JP2010/054042
§ 371 (c)(1),
(2), (4) Date: Nov. 16, 2011

(87) PCT Pub. No.: WO2010/104128
PCT Pub. Date: Sep. 16, 2010

(65) Prior Publication Data
US 2012/0064148 A1 Mar. 15, 2012

(30) Foreign Application Priority Data
Mar. 11, 2009 (JP) .................................. 2009-058063

(51) Int. Cl.
*A61K 9/127* (2006.01)

(52) U.S. Cl.
CPC .................................. *A61K 9/1271* (2013.01)
USPC ........................................................ 424/450

(58) Field of Classification Search
CPC ..................................................... A61K 9/127
USPC ........................................................ 424/450
See application file for complete search history.

(56) References Cited

U.S. PATENT DOCUMENTS

| 2006/0002991 | A1 | 1/2006 | Essler et al. |
| 2007/0110798 | A1 | 5/2007 | Drummond et al. |
| 2008/0145413 | A1 | 6/2008 | Panzer et al. |
| 2010/0129430 | A1* | 5/2010 | Sofou ........................... 424/450 |

FOREIGN PATENT DOCUMENTS

| EP | 1 420 010 | * | 8/2002 |
| EP | 1764089 | A1 | 3/2007 |
| JP | 2005-526727 | A | 9/2005 |
| JP | 2007-210953 | A | 8/2007 |
| JP | 2009-507876 | A | 2/2009 |
| WO | WO 2006/048329 | A1 | 5/2006 |

(Continued)

OTHER PUBLICATIONS

Extended European Search Report issued Aug. 5, 2013, in European Patent Application No. 10750881.4.

(Continued)

*Primary Examiner* — Gollamudi Kishore
(74) *Attorney, Agent, or Firm* — Birch, Stewart, Kolasch & Birch, LLP

(57) ABSTRACT

The present invention provides pH-responsive liposomes which are capable of holding a desired substance in an acidic pH environment and releasing the desired substance in a basic pH environment.

The present invention uses pH-responsive liposomes comprising, as constituent lipids thereof, a cationic amphiphilic molecule and at least one of an anionic amphiphilic molecule and a twitterionic amphiphilic molecule, wherein the liposomes, when dispersed in an aqueous medium, have a positive zeta potential in an acidic environment where the dispersion has a pH of less than 6.5 and have a negative zeta potential in a basic environment where the dispersion has a pH of 8.5 or more.

9 Claims, 3 Drawing Sheets

(56) References Cited

FOREIGN PATENT DOCUMENTS

| WO | 2006/118327 A1 | 11/2006 |
| WO | WO 2007/064857 A2 | 6/2007 |
| WO | 2008/143339 A1 | 11/2008 |
| WO | WO 2009/047006 A2 | 4/2009 |
| WO | WO 2009/051712 A1 | 4/2009 |

OTHER PUBLICATIONS

International Seach Report for PCT/JP2010/054042, mailed on Apr. 6, 2010.

G. Shi et al., "Efficient intracellular drug and gene delivery using folate receptor-targeted pH-sensitive liposomes composed of cationic/anionic lipid combinations", Journal of Controlled Release, vol. 80, 2002, pp. 309-319.

J. Boomer et al., "Acid-Triggered Release from Sterically Stabilized Fusogenic Liposomes via a Hydrolytic DePEGylation Strategy", Langmuir, vol. 19, 2003, pp. 6408-6415.

N. Duzgunes et al., "Proton-Induced Fusion of Oleic Acid-Phosphatidylethanolamine Liposomes", Biochemistry, vol. 24, 1985, pp. 3091-3098.

V. Budker et al., "pH-sensitive, cationic liposomes: A new synthetic virus-like vector", Nature Biotechnology, vol. 14, Jun. 1996, pp. 760-764.

Y. Obata et al., "Evaluation of pH-sensitive liposomes composed of the zwitterionic lipids for constructing injectable drug delivery system", Symposium on Macromolecules Yokoshu, vol. 57, No. 2, 2008, pp. 4942-4943, Japan.

Y. Sebyakin et al., "pH-Sensitive Cationic Lipopeptides for the Design of Drug-Delivery Systems", Russian Journal of Bioorganic Chemistry, vol. 32, No. 5, 2006, pp. 407-412.

Y. Sebyakin et al., "Structural and Functional Diversity of Artificial Membranes Based on Cationic Lipodipeptides", Biologicheskie Membrany, vol. 24, No. 3, 2007, pp. 259-265.

\* cited by examiner

PH-RESPONSIVE LIPOSOME

TECHNICAL FIELD

The present invention relates to pH-responsive liposomes which are capable of controlling the hold and release of a desired substance in response to changes in the pH environment. More specifically, the present invention relates to pH-responsive liposomes which are capable of holding a desired substance in an acidic pH environment and releasing the desired substance in a basic pH environment.

BACKGROUND ART

To control the release of a desired substance encapsulated within a molecular assembly such as liposomes, pH-responsive properties are commonly used. By way of example, liposomes based on phosphatidylethanolamine phospholipids are known (see, e.g., D. Papahadjopoulos et al., Biochemistry, 24 (1985) 3091-3098 (Non-patent Document 1), D. H. Thompson et al., Langmuir, 19 (2003) 6408-6415 (Non-patent Document 2)). This is based on the properties of phosphatidylethanolamine phospholipids which change their assembled structure in response to pH to thereby cause a change in their membrane permeability for a desired substance. However, liposomes containing dioleoylphosphatidylethanolamine (DOPE) can release the substance encapsulated therein only in an acidic environment (at pH 5 or less).

In addition, liposomes prepared from a mixture of anionic and cationic lipids are also known as pH-responsive liposomes (see G. Shi et al., Journal of Controlled Release 80 (2002) 309-319 (Non-patent Document 3)). However, this document fails to disclose that these liposomes release the substance encapsulated therein in a basic pH environment. Moreover, didecyldimethylammonium bromide (DDAB) having a quaternary amino group is used as a constituent member, and hence the liposomes are not intended to control the release of the encapsulated substance through ionization of amino groups. Further, there is a problem in that conventionally known cationic lipids are not suitable for administration to the human body because of their high cytotoxicity.

The inventors of the present invention have already found that liposomes which comprise, as a constituent lipid thereof, an amphiphilic molecule having a twitterionic functional group in its hydrophilic moiety hold a desired substance within their inner aqueous phase in a physiological pH environment and release the desired substance in an acidic pH environment (see JP 2007-210953 A (Patent Document 1) and WO2008/143339 (Patent Document 2)).

However, any pH-responsive molecular assembly has not yet been obtained, which holds a desired substance in an acidic pH environment and releases the desired substance in a basic pH environment.

In recent years, studies have been conducted to introduce a gene into cells by being conjugated with a cationic lipid alone or with a liposome containing the same. The inventors of the present invention have also developed a complex lipid suitable for such a purpose, which is low in cytotoxicity, is easy to synthesize and has a cationic functional group derived from an amino acid, and the inventors have also reported that such a complex lipid provides a formulation with high intracellular migration capability (see WO2006/118327 (Patent Document 3)).

PRIOR ART

Patent Documents

Patent Document 1: JP 2007-210953 A
Patent Document 2: WO2008/143339
Patent Document 3: WO2006/118327

Non-Patent Documents

Non-patent Document 1: D. Papahadjopoulos et al., Biochemistry, 24 (1985) 3091-3098
Non-patent Document 2: D. H. Thompson et al., Langmuir, 19 (2003) 6408-6415
Non-patent Document 3: G. Shi et al., Journal of Controlled Release 80 (2002) 309-319

DISCLOSURE OF THE INVENTION

Problem to be Solved by the Invention

As described above, any pH-responsive molecular assembly has not yet been known, which is capable of holding a desired substance in an acidic pH environment and releasing the desired substance in a basic pH environment. If it is possible to obtain a pH-responsive molecular assembly having such a release behavior, pH-responsive liposome formulations can be expected to have a much wider range of applications.

Means to Solve the Problem

As a result of extensive and intensive efforts made to achieve the above object, the inventors of the present invention have found that when liposomes comprising, as constituent lipids thereof, a cationic amphiphilic molecule and at least one of an anionic amphiphilic molecule and a twitterionic amphiphilic molecule are dispersed in an aqueous medium, the liposomes have a positive zeta potential in an acidic pH environment and have a negative zeta potential in a basic pH environment, and the liposomes release the desired substance held therein when their zeta potential changes from positive to negative with increase in the pH of the dispersion. This finding led to the completion of the present invention.

Namely, the present invention provides pH-responsive liposomes and a method for their preparation, as shown below.

[1] A pH-responsive liposome comprising a cationic amphiphilic molecule and at least one of an anionic amphiphilic molecule and a twitterionic amphiphilic molecule, wherein the liposome, when dispersed in an aqueous medium, has a positive zeta potential in an acidic environment where the dispersion has a pH of less than 6.5, and has a negative zeta potential in a basic environment where the dispersion has a pH of 8.5 or more.

[2] The pH-responsive liposome according to [1] above, which holds a desired substance in an acidic environment where the dispersion has a pH of less than 6.5, and releases the desired substance in a basic environment where the dispersion has a pH of 8.5 or more.

[3] The pH-responsive liposome according to [1] or [2] above, which comprises the cationic amphiphilic molecule in an amount of 5 to 95 mol % relative to the total number of moles of constituent lipids in the liposome, and comprises the anionic amphiphilic molecule and/or the twitterionic amphiphilic molecule in a total amount of 5 to 95 mol % relative to the total number of moles of constituent lipids in the liposome.

[4] The pH-responsive liposome according to any one of [1] to [3] above, wherein the zeta potential of the pH-responsive liposome changes from positive to negative with increase in the pH of the dispersion within a range of pH 7.0 or more to less than pH 8.0.

[5] The pH-responsive liposome according to any one of [1] to [4] above, which releases the desired substance held therein when the zeta potential changes from positive to negative.

[6] The pH-responsive liposome according to any one of [1] to [5] above, wherein the cationic amphiphilic molecule comprises a cationic functional group which is easy to ionize in an acidic environment where the dispersion has a pH of less than 6.5 and is difficult to ionize in a basic environment where the dispersion has a pH of 8.5 or more.

[7] The pH-responsive liposome according to [6] above, wherein the cationic functional group is selected from the group consisting of an amino group, a guanidino group, an imidazole group and derivatives thereof.

[8] The pH-responsive liposome according to any one of [1] to [7] above, which comprises, as a constituent lipid thereof, at least one of cationic amphiphilic molecules represented by the following formulae:

[Formula 1]

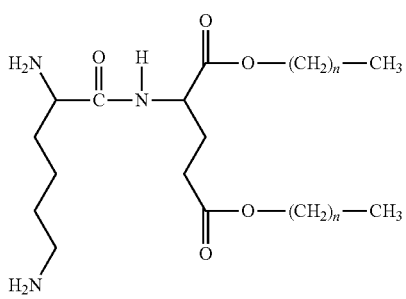

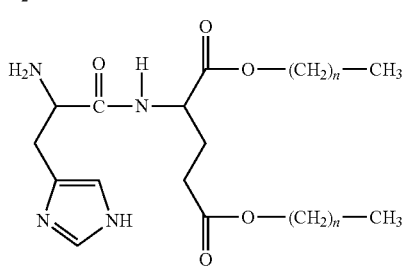

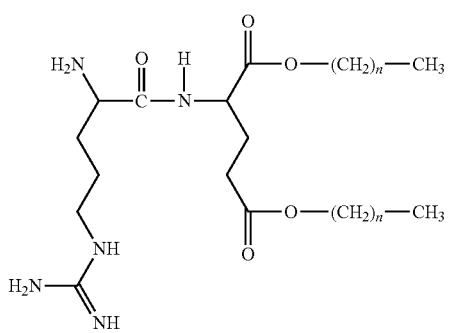

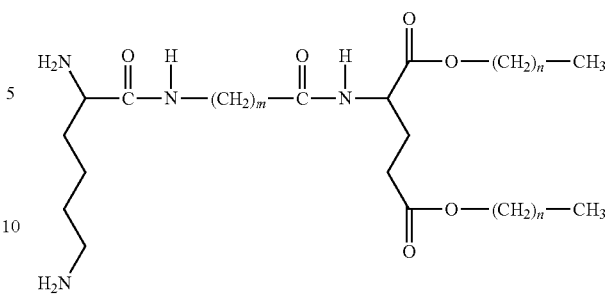

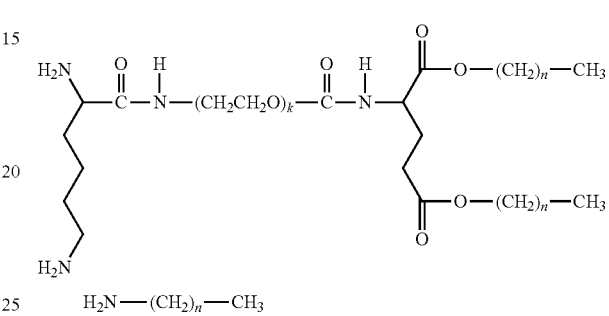

$H_2N-(CH_2)_n-CH_3$

[wherein each n is independently an integer of 8 to 22, and m and k are each independently an integer of 1 to 14].

[9] The pH-responsive liposome according to any one of [1] to [8] above, which comprises, as a constituent lipid thereof, at least one of anionic amphiphilic molecules or twitterionic amphiphilic molecules represented by the following formulae:

[Formula 2]

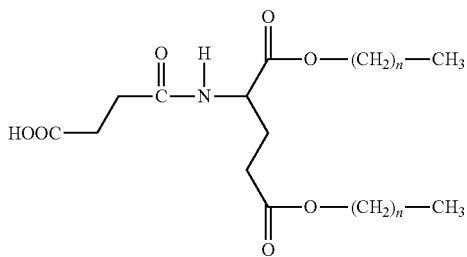

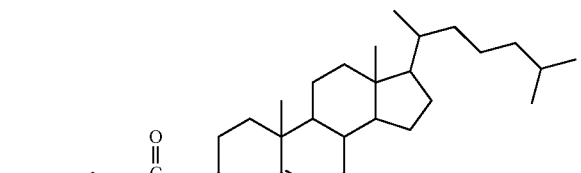

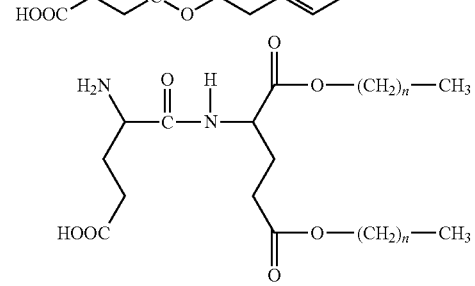

-continued

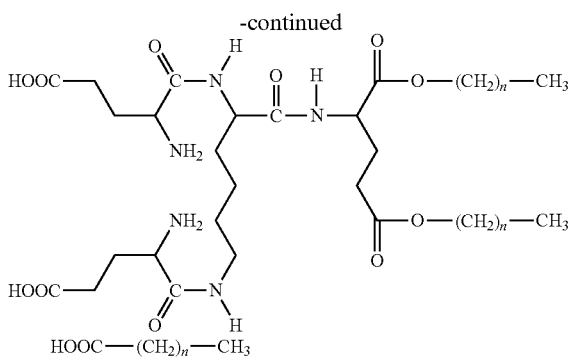

[wherein each n is independently an integer of 8 to 22].

[10] The pH-responsive liposome according to any one of [1] to [9] above, which comprises a cholesterol molecule in an amount of 0.01 to 30 mol % relative to the total number of moles of constituent lipids in the liposome.

[11] The pH-responsive liposome according to any one of [1] to [10] above, which comprises a polyethylene glycol-linked amphiphilic molecule in an amount of 0.1 to 50 mol % relative to the total number of moles of constituent lipids in the liposome.

Effect of the Invention

The present invention enables the provision of pH-responsive liposomes which have a positive zeta potential in an acidic environment where a dispersion of the liposomes has a pH of less than 6.5 and have a negative zeta potential in a basic environment where the dispersion has a pH of 8.5 or more. According to a preferred embodiment of the present invention, the pH-responsive liposomes of the present invention are capable of holding a desired substance in an acidic pH environment and releasing the desired substance in a basic pH environment.

BEST MODES FOR CARRYING OUT THE INVENTION

Figure 1:
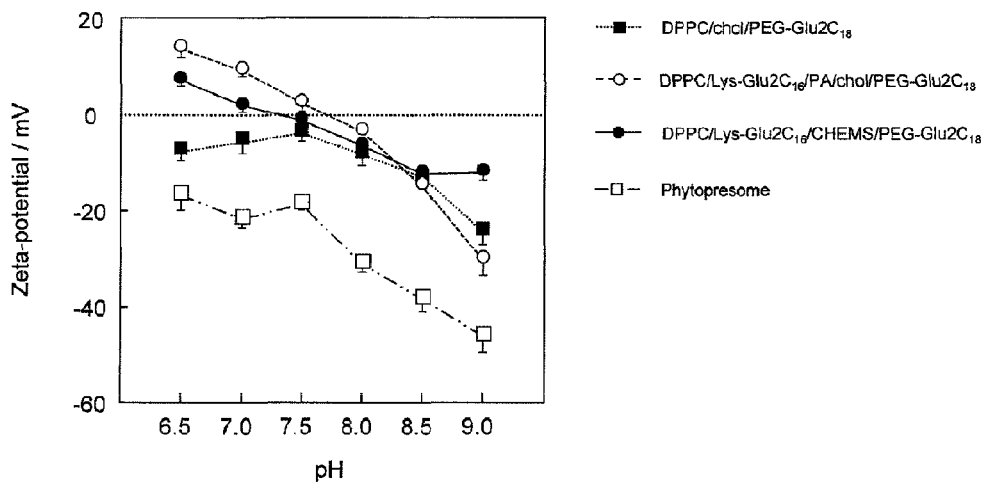
FIG. 1 is a graph showing the results of zeta potential measured for the pH-responsive liposomes obtained in the Example section.

The pH-responsive liposomes of the present invention and a method for their preparation will be described in more detail below.

The pH-responsive liposomes of the present invention comprise a cationic amphiphilic molecule and at least one of an anionic amphiphilic molecule and a twitterionic amphiphilic molecule, wherein the liposomes, when dispersed in an aqueous medium, have a positive zeta potential in an acidic environment where the dispersion has a pH of less than 6.5 and have a negative zeta potential in a basic environment where the dispersion has a pH of 8.5 or more. Namely, in the pH-responsive liposomes of the present invention, their zeta potential changes from positive to negative with increase in the pH of the dispersion within a range of pH 6.5 or more to less than pH 8.5. In a preferred embodiment of the present invention, the zeta potential in the pH-responsive liposomes of the present invention changes from positive to negative with increase in the pH of the dispersion within a range of pH 7.0 or more to less than pH 8.0.

Constituent lipids in the pH-responsive liposomes of the present invention and a method for preparing the pH-responsive liposomes will be described below.

Cationic Amphiphilic Molecules

Any cationic amphiphilic molecule may be used in the present invention as long as it is an amphiphilic molecule having a cationic functional group in its hydrophilic moiety. Such a cationic amphiphilic molecule preferably contains a cationic functional group which is easy to ionize in an acidic environment where the dispersion has a pH of less than 6.5 and is difficult to ionize in a basic environment where the dispersion has a pH of 8.5 or more. For example, it is preferred that 90% or more of the cationic functional groups contained in the membrane components are ionized in an acidic environment where the dispersion has a pH of less than 6.5, while 50% or less of the cationic functional groups contained in the membrane components are ionized in a basic environment where the dispersion has a pH of 8.5 or more.

As used herein, the term "cationic functional group" is intended to mean any group showing cationic properties in an aqueous solution. In terms of bio compatibility, preferred are groups derived from amino acids, and particularly preferred are an amino group, a guanidino group, an imidazole group and derivatives thereof.

Examples of such "derivatives" include compounds in which a hydrogen atom(s) contained in an amino group, a guanidino group or an imidazole group is/are replaced with a substituent(s), such as a lower alkyl group (e.g., methyl, ethyl, propyl, isopropyl, n-butyl, sec-butyl), an aminoalkyl group (e.g., aminomethyl, aminoethyl, aminopropyl, aminobutyl) or a corresponding oligoaminoalkyl group, a hydroxyl group, a hydroxyalkyl group (e.g., hydroxymethyl, hydroxyethyl, hydroxypropyl), or an oligooxyalkyl group (e.g., oligooxymethyl, oligooxyethyl, oligooxypropyl). The number of substituents is not limited in any way.

The number of cationic functional groups contained in the cationic amphiphilic molecule is not limited in any way. Although the cationic amphiphilic molecule may have one or several cationic functional groups, one or two cationic functional groups are preferred because starting materials are readily available. In cases where the cationic amphiphilic molecule contain several cationic functional groups, they may be either the same or different.

Cationic amphiphilic molecules preferred for use are compounds represented by formulae (I-a) to (I-c):

[Formula 3]

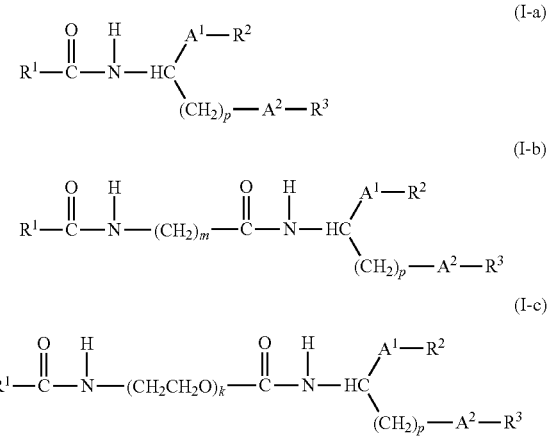

[wherein each $R^1$ is independently a hydrocarbon group having a cationic functional group derived from an amino acid, $R^2$ and $R^3$ are each independently an open-chain hydrocarbon group, $A^1$ and $A^2$ are each independently a linker selected from the group consisting of —COO—, —OCO—, —CONH— and NHCO—, each p is independently an integer of 2 to 4, m is an integer of 1 to 14, and k is an integer of 1 to 250].

Compounds represented by the above formulae (I-a) to (I-c) are easy to synthesize from readily available starting materials, and have high liposome-forming ability to thereby stably hold a desired substance within the inner aqueous phase of the resulting liposomes. Moreover, these compounds are also advantageous in that they are highly biodegradable and are also less toxic because their degraded products are amino acids or derivatives thereof, or long-chain alcohols, etc.

In the above formulae, each $R^1$ is independently a hydrocarbon group having a cationic functional group derived from an amino acid.

$R^1$ may have at least one cationic functional group, preferably two or more cationic functional groups. In particular, compounds having two or more cationic functional groups are preferred because of their strong electrostatic interactions with in vivo tissues or cells in a physiological environment. In the case of having two or more cationic substituents, these cationic substituents may be selected in any combination.

For example, $R^1$ is preferably a group represented by the following formula (a), (b) or (c).

[Formula 4]

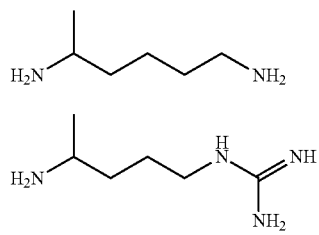

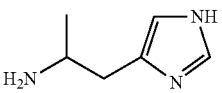

In the above formulae, $R^2$ and $R^3$ are each independently an open-chain hydrocarbon group. The term "open-chain hydrocarbon group" is intended to mean any hydrophobic group as long as it can be introduced into the linker $A^1$ or $A^2$ through covalent bonding. Such an open-chain hydrocarbon group may be either linear or branched, preferably linear. The number of carbon atoms in the main chain of such an open-chain hydrocarbon group is preferably 12 to 30, more preferably 12 to 22. When such an open-chain hydrocarbon group has an unsaturated bond such as a double bond or a triple bond, the number of unsaturated bonds is preferably 1 to 4. The main chain of such an open-chain hydrocarbon group is preferably an alkyl chain, an alkenyl chain or an alkynyl chain, more preferably an alkyl chain.

Such an open-chain hydrocarbon group may have a substituent(s) selected from the group consisting of an alkyl group, an alkenyl group, an alkynyl group, an isoprenoid group, a carboxyl group, a hydroxyl group, an amino group, and a mercapto group. In this case, a preferred alkyl group is an alkyl group containing 1 to 6 carbon atoms, and examples include a methyl group, an ethyl group, a propyl group, an isopropyl group, a n-butyl group, a sec-butyl group, a tert-butyl group, a pentyl group, a hexyl group and so on. A preferred alkenyl group is an alkenyl group containing 1 to 6 carbon atoms, and examples include a vinyl group, an allyl group, a propenyl group, an isopropenyl group, a 2-butenyl group and so on. A preferred alkynyl group is an alkynyl group containing 1 to 6 carbon atoms, and examples include an ethynyl group, a propynyl group, a butynyl group and so on.

Among these open-chain hydrocarbon groups, preferred as $R^2$ and $R^3$ are optionally substituted alkyl chains containing 12 to 22 carbon atoms.

Likewise, in the above formulae, $A^1$ and $A^2$ are each independently a linker selected from the group consisting of —COO—, —OCO—, —CONH— and NHCO—. Although $A^1$ and $A^2$ may be selected in any combination, $A^1$ and $A^2$ are each preferably —COO— because starting materials are readily available.

In the above formulae, each p is independently an integer of 2 to 4, which is preferred in that if p is 2 to 4, open-chain hydrocarbon groups in a compound of formula (I) can be oriented almost perpendicular to the membrane plane in the resulting bimolecular membrane. In addition, if p is 2 to 4, cationic amphiphilic molecules are assembled in an aqueous solution to form a bimolecular membrane having a stable hydrophilic-hydrophobic interface, which facilitates the formation of a vesicular structure. Thus, the effect of stabilizing a vesicular structure and a dispersion state can be expected. In particular, p is more preferably 2 in terms of low cost and low toxicity because glutamic acid or a derivative thereof can be used as a starting material in this case.

In the above formulae, m is an integer of 1 to 14. m is preferably 1 to 11, more preferably 1 to 8, and even more preferably 1 to 5.

Likewise, in the above formulae, k is an integer of 1 to 250. k is more preferably 1 to 120, and even more preferably 1 to 10.

Specific examples of compounds represented by the above formulae (I-a) to (I-c) preferably include compounds represented by the following formulae:

[Formula 5]

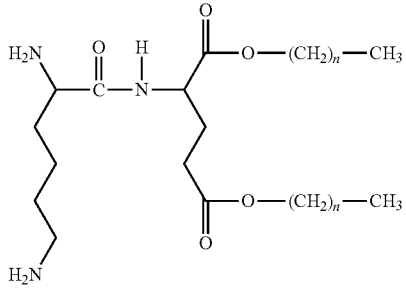
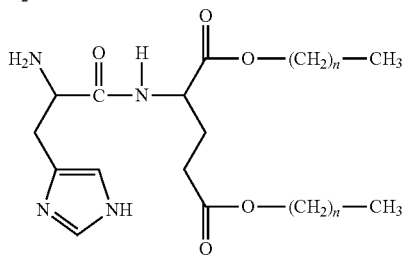
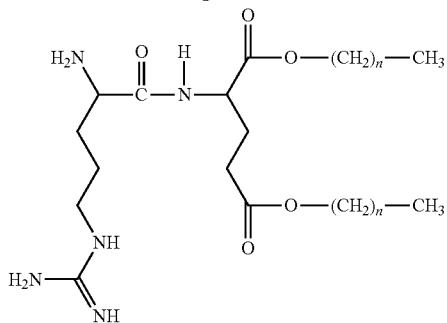
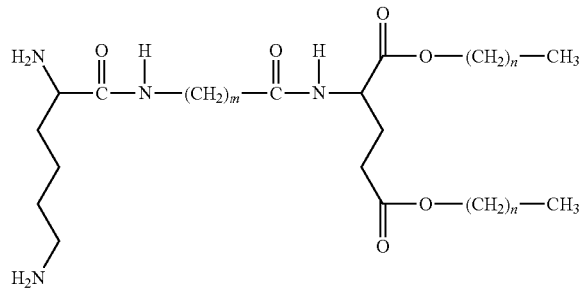
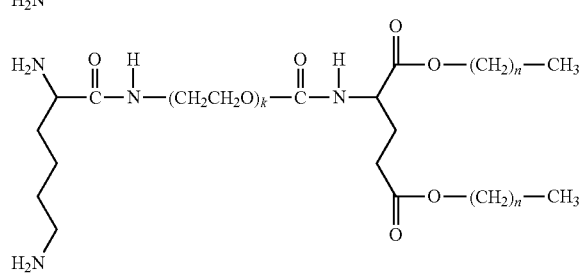

[wherein each n is independently an integer of 7 to 21, m is an integer of 1 to 14, and k is an integer of 1 to 250].

Compounds represented by the above formulae (I-a) to (I-c) can be prepared in a simple manner by combining known reactions. For example, a trifunctional core compound having the following formula:

[Formula 6]

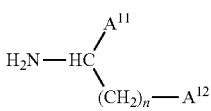

[wherein $A^{11}$ and $A^{12}$ are each independently a carboxyl group, a hydroxyl group or an amino group, and n is an integer of 2 to 4]

may be reacted sequentially with a source of open-chain hydrocarbon groups and a source of hydrocarbon groups having a cationic functional group. It should be noted that reference may be made to WO2006/118327 for detailed procedures of preparation.

These cationic amphiphilic molecules may be used either alone or in combination.

Cationic amphiphilic molecules used in the present invention preferably comprise at least one member selected from a group of compounds represented by the following formulae:

[Formula 7]

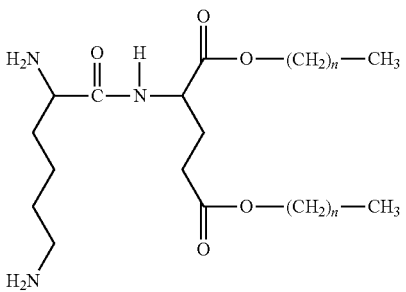
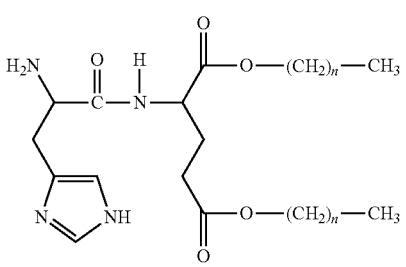
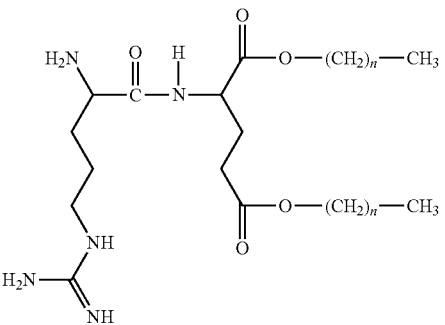

-continued

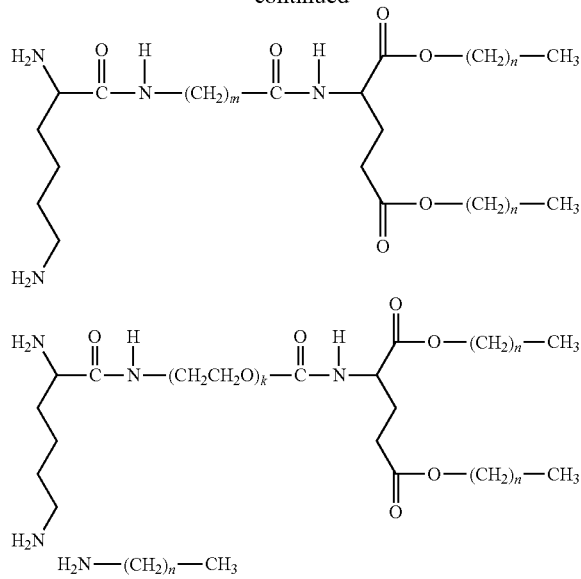

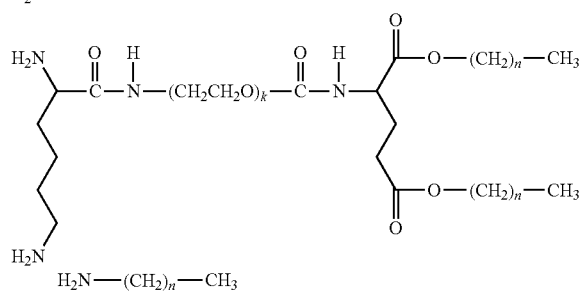

[wherein each n is independently an integer of 8 to 22, m is an integer of 1 to 14, and k is an integer of 1 to 250].

In the above formulae, n is preferably 11 to 21, more preferably 11 to 17, and even more preferably 13 to 17. m is preferably 1 to 11, more preferably 1 to 8, and even more preferably 1 to 5. k is preferably 1 to 250, more preferably 1 to 120, and even more preferably 1 to 10.

In the pH-responsive liposomes of the present invention, the content of cationic amphiphilic molecules is preferably 5 mol % or more, more preferably 10 mol % or more, and even more preferably 30 mol % or more, relative to the total number of moles of constituent lipids in the liposomes. Moreover, the content is preferably 95 mol % or less, more preferably 80 mol % or less, even more preferably 50 mol % or less, and particularly preferably 30 mol % or less.

Anionic Amphiphilic Molecules

Any anionic amphiphilic molecule may be used in the present invention as long as it is an amphiphilic molecule having an anionic functional group in its hydrophilic moiety. As used herein, the term "anionic functional group" is intended to mean any group showing anionic properties in an aqueous solution in a basic pH environment. Preferred examples of such an anionic functional group include a carboxyl group and a phosphate group.

Specific examples of such an anionic amphiphilic molecule include diacylphosphatidylglycerol, diacylphosphatidic acid, diacylphosphatidylinositol, diacylphosphatidylserine, fatty acids, carboxylic acid-type amphiphilic molecules, anionic amino acid-type amphiphilic molecules and so on.

These anionic amphiphilic molecules may be used either alone or in combination.

Twitterionic Amphiphilic Molecules

Any twitterionic amphiphilic molecule may be used in the present invention as long as it is an amphiphilic molecule having both a cationic functional group and an anionic functional group in its hydrophilic moiety.

Preferred for use as a twitterionic amphiphilic molecule is a compound represented by formula (II):

[Formula 8]

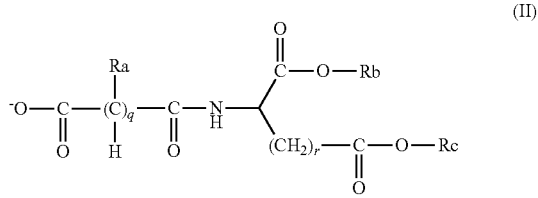

[wherein q and r are each independently an integer of 1 to 4, one of Ra is $NH_3^+$ and the others are each a hydrogen atom, and Rb and Rc are each independently an open-chain hydrocarbon group containing 8 to 22 carbon atoms].

In formula (II), q and r are preferably each independently 2 or 3. Likewise, although one of Ra is $NH_3^+$ and the others are each a hydrogen atom, it is preferred that Ra on the third or fourth carbon from the terminal carboxyl group is $NH_3^+$ and the others are each a hydrogen atom. More specifically, preferred examples include twitterionic amphiphilic molecules of formula (II) in which q is 3, r is 3, Ra on the fourth carbon from the terminal carboxyl carbon is $NH_3^+$ and the others are each H; in which q is 2, r is 3, Ra on the third carbon from the terminal carboxyl carbon is $NH_3^+$ and the others are each H; in which q is 3, r is 2, Ra on the fourth carbon from the terminal carboxyl carbon is $NH_3^+$ and the others are each H; and in which q is 2, r is 2, Ra on the third carbon from the terminal carboxyl carbon is $NH_3^+$ and the others are each H.

Rb and Rc are each independently an open-chain hydrocarbon group containing 8 to 22 carbon atoms. The term "open-chain hydrocarbon group" is intended to mean any hydrophobic group as long as it can be introduced through covalent bonding. Such an open-chain hydrocarbon group may be either linear or branched, preferably linear. In addition, such an open-chain hydrocarbon group may have a substituent(s) selected from the group consisting of an alkyl chain, an alkenyl chain, an alkynyl chain, an isoprenoid chain, a vinyl group, a carboxyl group, a hydroxyl group, an amino group, and a mercapto group. The number of carbon atoms in such an open-chain hydrocarbon group is preferably 12 to 20, more preferably 14 to 18. Moreover, such an open-chain hydrocarbon group may have an unsaturated bond such as a double bond or a triple bond, and in this case, the number of unsaturated bonds is preferably 1 to 4. Among these examples, preferred as Rb and Rc are linear or branched alkyl groups containing 12 to 20 carbon atoms, with linear alkyl groups containing 14 to 18 carbon atoms being particularly preferred.

Compounds represented by the above formula (II) can be prepared by the method described in JP 2007-210953 A or an equivalent method thereof. For detailed procedures of preparation, reference may be made to JP 2007-210953 A.

These twitterionic amphiphilic molecules may be used either alone or in combination.

In the present invention, an anionic amphiphilic molecule and a twitterionic amphiphilic molecule may be used in combination, or alternatively, only one of these two types of molecules may be used. In the present invention, by comprising at least one of an anionic amphiphilic molecule and a twitterionic amphiphilic molecule as a constituent lipid, the assembled state of molecules constituting a liposome will change in a weakly basic environment to cause a change in the membrane permeability of the liposome, whereby the encapsulated desired substance can be released.

Above all, the pH-responsive liposomes of the present invention preferably comprise, as a constituent lipid thereof, at least one of anionic amphiphilic molecules and twitterionic amphiphilic molecules represented by the following formulae:

[Formula 9]

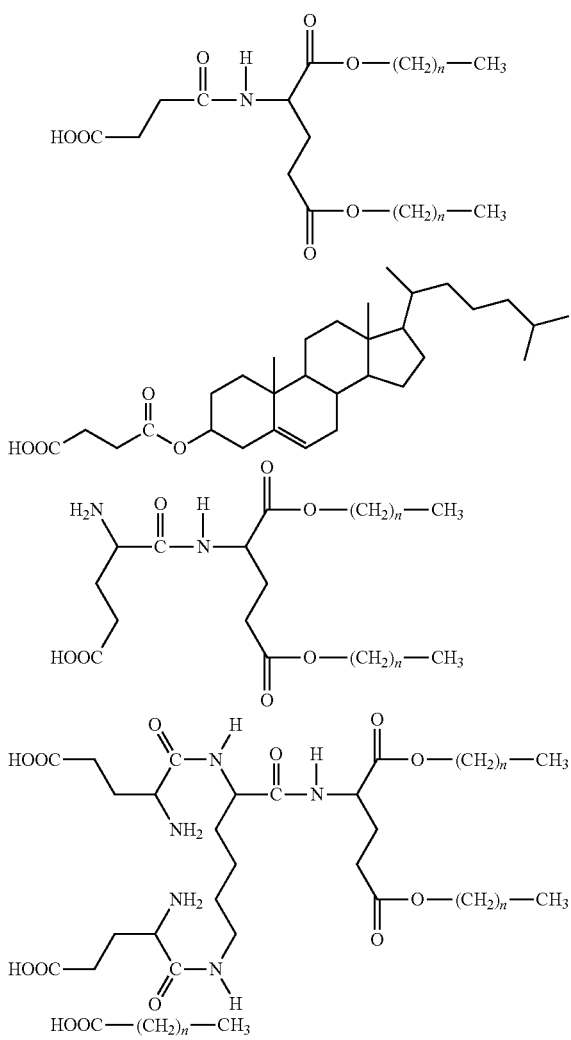

[wherein each n is independently an integer of 8 to 22].

These compounds are known, and cholesteryl hemisuccinate (CHEMS) and hexacosanoic acid (where n is 24) are readily available from Sigma-Aldrich (St. Louis, Mo., USA).

In the pH-responsive liposomes of the present invention, the content of anionic amphiphilic molecules and twitterionic amphiphilic molecules is preferably 5 mol % or more, more preferably 10 mol % or more, and even more preferably 30 mol % or more, relative to the total number of moles of constituent lipids in the liposomes. Moreover, the content is preferably 95 mol % or less, more preferably 80 mol % or less, even more preferably 50 mol % or less, and particularly preferably 30 mol % or less.

When anionic amphiphilic molecules and twitterionic amphiphilic molecules are used in combination, the mixing molar ratio between anionic amphiphilic molecules and twitterionic amphiphilic molecules (i.e., anionic amphiphilic molecules/twitterionic amphiphilic molecules) is preferably 10/1 to 1/10, more preferably 5/1 to 1/5, and even more preferably 2/1 to 1/2

The pH-responsive liposomes of the present invention may further comprise a steroid member. Examples of such a steroid member include all steroid members having perhydrocyclopentanophenanthrene, such as sterols, bile acid, provitamin D, steroid hormones and so on. Among them, sterols are preferred for use. Examples of sterols include ergosterol, cholesterol and so on. Among them, cholesterol molecules are preferred.

The content of steroid members is not limited in any way, but it is preferably 0.01 mol % or more, more preferably 0.05 mol % or more, and even more preferably 0.1 mol % or more, relative to the total number of moles of constituent lipids in the liposomes. Moreover, the content is preferably 30 mol % or less, more preferably 10 mol % or less, and even more preferably 5 mol % or less. Steroid members can serve as stabilizers for molecular assemblies and may be adjusted as appropriate, e.g., depending on the desired release velocity and release rate. These steroid members may be used either alone or in combination.

Moreover, the pH-responsive liposomes of the present invention may further comprise a polyethylene glycol-linked amphiphilic molecule. Any polyethylene glycol-linked amphiphilic molecule may be used in the present invention as long as it is an amphiphilic molecule having polyethylene glycol linked to its hydrophilic moiety. The polyethylene glycol moiety preferably has a molecular weight of about 200 to about 50,000, more preferably about 1000 to about 10,000.

Preferred for use as a polyethylene glycol-linked amphiphilic molecule is a compound represented by the following formula (III), by way of example:

[Formula 10]

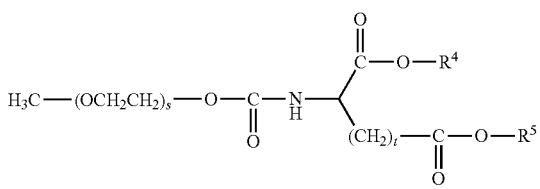

(III)

[wherein s is an integer of 3 to 250, t is an integer of 1 to 4, and $R^4$ and $R^5$ are each independently an open-chain hydrocarbon group containing 8 to 22 carbon atoms].

In the above formula (III), s may be selected such that the molecular weight of the polyethylene glycol moiety is within the above range. Likewise, t is preferably 2 or 3. Specific examples of an open-chain hydrocarbon groups as $R^4$ or $R^5$ include the same groups as listed for Rb and Rc in formula (II).

By comprising such a polyethylene glycol-linked amphiphilic molecule, the liposomes will be prevented from aggregating to thereby increase their retention time in blood after in vivo administration. Polyethylene glycol-linked amphiphilic molecules may be used either alone or in combination.

In the present invention, the content of polyethylene glycol-linked amphiphilic molecules is not limited in any way, but it is preferably 0.1 mol % or more, more preferably 0.2 mol % or more, and even more preferably 0.3 mol % or more, relative to the total number of moles of constituent lipids in the liposomes. Moreover, the content is preferably 50 mol % or less, more preferably 10 mol % or less, and even more preferably 5 mol % or less.

The pH-responsive liposomes of the present invention may comprise not only the above components, but also additional one or more phospholipids known as constituent lipids of liposomes (e.g., egg yolk lecithin, soybean lecithin, hydrogenated egg yolk lecithin, hydrogenated soybean lecithin, diacylphosphatidylcholine, diacylphosphatidylethanolamine, sphingomyelin, many types of glycolipids) within a range where the purpose of the present invention is not impaired.

The pH-responsive liposomes of the present invention may be prepared in any manner according to known procedures. For example, a powder or thin film of a lipid mixture containing a cationic amphiphilic molecule, at least one of an anionic amphiphilic molecule and a twitterionic amphiphilic molecule, and other optional components may be hydrated and dispersed, followed by high pressure extrusion, ultrasonication, agitation (vortex mixing, homogenizer), high speed agitation, French press, freeze thawing, microfluidizer or other techniques to prepare pH-responsive liposomes. In another embodiment, the above lipid mixture may be dissolved in an organic solvent, and the resulting solution may be injected into an aqueous phase and then treated under reduced pressure or dialyzed to remove the organic solvent (e.g., ethanol or ether), thereby preparing pH-responsive liposomes. In yet another embodiment, the above lipid mixture may be dispersed in an aqueous phase together with a nonionic surfactant (e.g., sodium cholate, sodium dodecyl sulfate, Triton X, octylglycoside or lauryl ether) to form an emulsion, followed by dialysis to prepare pH-responsive liposomes. In other embodiments, reversed-phase evaporation, incubation or other techniques may be used to prepare pH-responsive liposomes.

The thus obtained pH-responsive liposomes of the present invention are capable of having a positive zeta potential in an acidic environment where the liposome dispersion has a pH of less than 6.5 and having a negative zeta potential in a basic environment where the dispersion has a pH of 8.5 or more. Namely, in the pH-responsive liposomes of the present invention, their zeta potential changes from positive to negative with increase in the pH of the liposome dispersion within a range of pH 6.5 or more to less than pH 8.5. More preferably, the zeta potential in the pH-responsive liposomes of the present invention changes from positive to negative with increase in the pH of the liposome dispersion within a range of pH 7.0 or more to less than pH 8.0.

According to a preferred embodiment of the present invention, the pH-responsive liposomes of the present invention have such a surface charge behavior in response to changes in pH, and hence are capable of holding a desired substance in an acidic environment where the liposome dispersion has a pH of less than 6.5 and releasing the desired substance in a basic environment where the dispersion has a pH of 8.5 or more. According to a more preferred embodiment of the present invention, the pH-responsive liposomes of the present invention are capable of holding a desired substance when the above dispersion has a pH of less than 7.0 and releasing the desired substance when the above dispersion has a pH of 8.0 or more.

As used herein, the phrase "holding a desired substance" is intended to mean that the desired substance is held in a state dispersed in water within the inner aqueous phase of liposomes, although only a slight amount (preferably less than 10%) of the desired substance may be released. For example, in the case of using calcein which is a fluorescent substance, its release rate after 1 hour is preferably less than 10%, more preferably less than 5%. It should be noted that the release rate of calcein can be determined by the following equation.

$$\text{Release rate of calcein}(\%) = (I_x - I_0)/(I_T \times 1.1 - I_0) \qquad \text{[Equation 1]}$$

$I_0$: fluorescence intensity at pH 6.5
$I_x$: fluorescence intensity after addition to buffer at each pH
$I_T$: fluorescence intensity upon addition of 200 μL 1% Triton-X In addition, the phrase "releasing the desired substance" is intended to mean that preferably 10% or more of the desired substance is released within 1 hour after changing the pH of the outer aqueous phase. For example, the release rate of calcein determined by the above equation is preferably 10% or more, more preferably 20% or more.

Procedures used to hold a desired substance in liposomes may be selected as appropriate, depending on the type of desired substance, etc. For example, when the desired substance is a water-soluble drug, the drug may be dissolved in an aqueous phase during liposome preparation. Molecules of the water-soluble drug which are not held may be separated from the liposomes holding the desired substance by gel filtration, ultracentrifugation or ultrafiltration membrane treatment, etc. On the other hand, when the desired substance is a fat-soluble drug, a lipid mixture in a state dissolved in an organic solvent may be mixed with the drug and treated in the same manner as described above to form liposomes, whereby the desired substance can be held, e.g., in the hydrophobic moiety of bimolecular membrane vesicles. When the desired substance is a probe, a nucleic acid, a protein or the like, the desired substance may be held within liposomes in the same manner or may be localized on the outer surface of bimolecular membrane vesicles.

When dispersed in an aqueous medium, the pH-responsive liposomes of the present invention can show a pH-responsive behavior never before possible, i.e., have a positive zeta potential in an acidic pH environment and have a negative zeta potential in a basic pH environment. By holding a desired substance in the pH-responsive liposomes of the present invention, pH-responsive formulations can be expected to have a wider range of applications.

The present invention will be further described in more detail by way of the following illustrative examples, which are not intended to limit the scope of the invention.

Example 1

[1] Preparation of Lipid Mixtures

Each lipid mixture indicated in Table 1 was dissolved in t-butyl alcohol and then lyophilized to prepare a lipid mixture powder. The cationic amphiphilic molecule used was 1,5-dihexadecyl N-lysyl-L-glutamate (Lys-Glu2C$_{16}$), while the anionic amphiphilic molecule used was cholesteryl hemisuccinate (CHEMS) or palmitic acid (PA). The amount of modification with PEG5000-GLu2C18 was set to 0.3 mol % of the total lipids. The chemical structures of the lipids used are shown below.

TABLE 1

| Lipid mixture | Mixing ratio (mol) |
|---|---|
| DPPC/chol/PEG$_{5000}$-Glu2C$_{18}$ | 5/5/0.03 |
| DPPC/Lys-Glu2C$_{16}$/PA/chol/PEG$_{5000}$-Glu2C$_{18}$ | 2.5/2.5/2.5/2.5/0.03 |
| DPPC/Lys-Glu2C$_{16}$/CHEMS/PEG$_{5000}$-Glu2C$_{18}$ | 5/2.5/2.5/0.03 |
| Phytopresome | — |

TABLE 1-continued

| Lipid mixture | Mixing ratio (mol) |
|---|---|

[Formula 11]

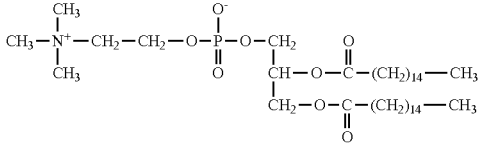

DPPC

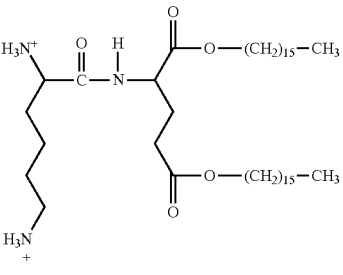

1,5-Dihexadecyl N-lysyl-L-glutamate
(Lys-Glu2C$_{16}$)

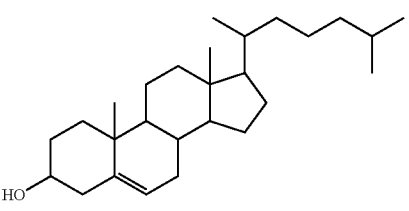

Cholesterol(chol)

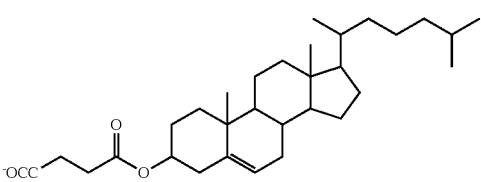

Cholesteryl hemisuccinate
(CHEMS)

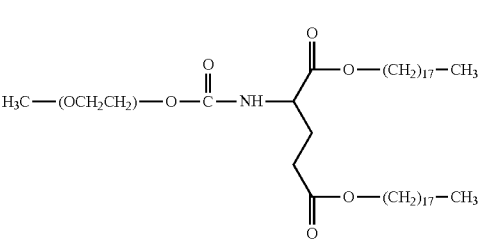

PEG-lipid (PEG: Mw 5000)

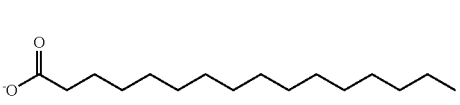

Palmitic acid (PA)

[2] Preparation of Liposomes

Each lipid mixture (20 mg) was dispersed in 20 mM phosphate buffer (1 mL, pH 6.5) and stirred for 6 hours, followed by high pressure extrusion (final pore size: 0.22 µm) to prepare liposomes having a particle size of 200 to 300 nm. The lipid concentration of the prepared liposomes was calculated from the DPPC concentration in the liposome dispersion.

[3] Measurement of Zeta Potential

The liposomes thus prepared (10 µL, [lipid]=10 mg/ml) were added to 990 µl of 20 mM Tris-buffer (pH 7.0, 7.5, 8.0, 8.5 or 9.0) at a final concentration [lipid]=1 mg/mL, and then measured for their zeta potential at 37° C. (Marvern Zetasizer). The results obtained are shown in FIG. 1.

As shown in FIG. 1, the liposomes prepared from DPPC/chol/PEG-Glu2C$_{18}$ showed a negative zeta potential at all pH values tested. Likewise, the liposomes of Phytopresome composition used as a control also showed a negative zeta potential at all pH values tested. These liposomes were both found to have a lower zeta potential at a pH of 7.4 or more. This would be because the anionic ionization tendency at the polar head of the hydrophilic moiety in phospholipids was enhanced with increase in pH.

In contrast, the pH-responsive liposomes of the present invention prepared from DPPC/Lys-Glu2C$_{16}$/PA/chol/PEG-Glu2C$_{18}$ or DPPC/Lys-Glu2C$_{16}$/CHEMS/PEG-Glu2C$_{18}$ showed a positive zeta potential at a pH value of 7.4 or 7.5 or less, and their zeta potential shifted to negative values at higher pH values. This change of zeta potential from positive to negative in response to increasing pH would be a phenomenon resulting from deprotonation of Lys-Glu2C$_{16}$ contained in the membrane components. Moreover, the behavior of zeta potential changes was found to vary depending on the type of anionic lipid.

[4] Measurement of Particle Size

The liposomes prepared above (10 µL each, [lipid]=10 mg/ml) were each added to 990 µl of 20 mM Tris-buffer (pH 7.0, 7.5, 8.0, 8.5 or 9.0) at a final concentration [lipid]=1 mg/mL, and then measured for their particle size by dynamic light scattering (BECKMAN COULTER N4 PLUS). The results obtained are shown in FIG. 2.

Figure 2:
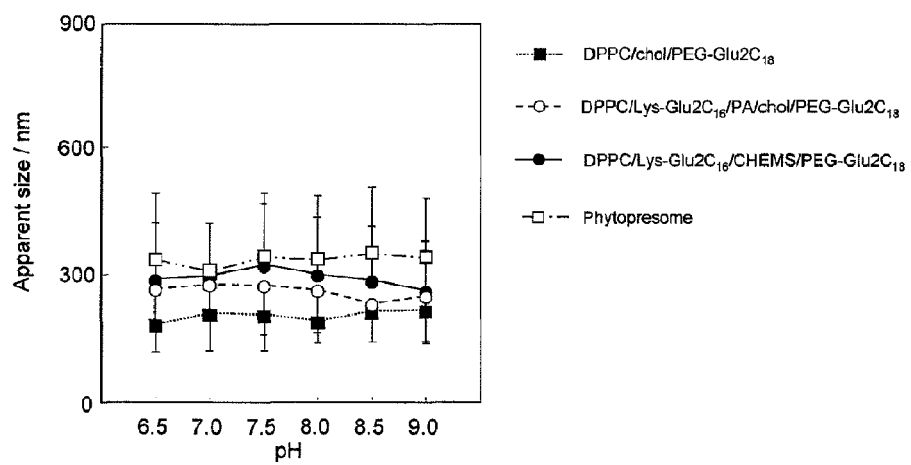
FIG. 2 is a graph showing the results of particle size measured for the pH-responsive liposomes obtained in the Example section.

As shown in FIG. 2, the prepared four types of liposomes had a particle size of about 200 to 300 nm, and were stable against pH changes because they showed no change in their particle size at all pH values tested. Thus, the particle size of the liposomes at each pH was substantially identical with their particle size when prepared at pH 6.5, and hence remained unchanged.

[5] Preparation of Calcein-Encapsulating Liposomes

To the four types of lipid mixtures (20 mg each), a 1 mM aqueous calcein solution (2 mL, pH 6.5) was added and stirred for hydration for 6 hours, followed by extrusion (final pore size: 0.22 µm) to prepare calcein-encapsulating liposomes having a particle size of about 200 nm. Unencapsulated calcein molecules were removed by gel filtration (Sephadex G-75).

[6] Release Behavior of Calcein

The four types of calcein-encapsulating liposomes thus prepared ([lipid]=1 mg/mL, 30 µL each) were each added to 570 µL of 20 mM Tris-buffer (pH 7.0, 7.5, 8.0, 8.5 or 9.0) and allowed to stand at 37° C. for 1 hour. These mixtures (100 µL each) were each diluted with 1.9 mL of 20 mM Tris-buffer (pH 6.5) and analyzed by fluorimetry ($\lambda_{ex}$: 490 nm, $\lambda_{em}$: 520 nm). The release rate of calcein was calculated by the following equation. The results obtained are shown in FIG. 3.

$$\text{Release rate of calcein}(\%) = (I_x - I_0)/(I_T \times 1.1 - I_0) \quad \text{[Equation 2]}$$

Figure 3:
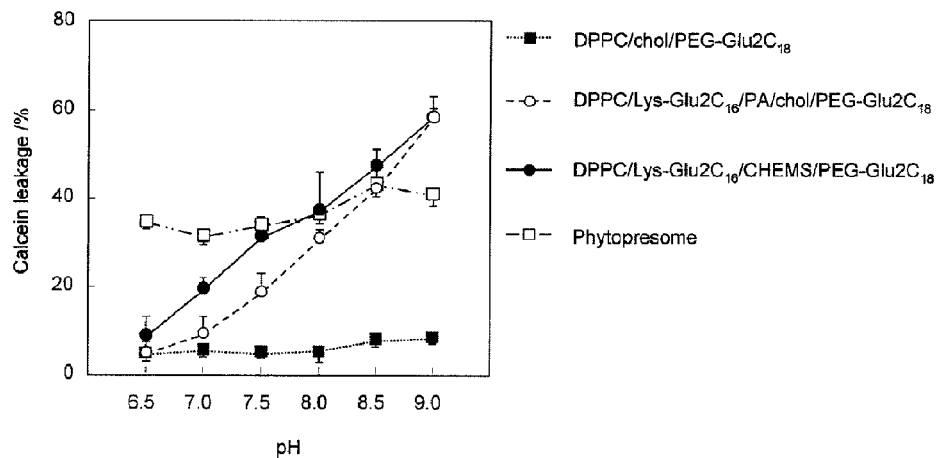
FIG. 3 is a graph showing the release behavior of calcein from the calcein-encapsulating liposomes obtained in the Example section.

$I_0$: fluorescence intensity at pH 6.5
$I_x$: fluorescence intensity after addition to buffer at each pH
$I_T$: fluorescence intensity upon addition of 200 µL 1% Triton-X As shown in FIG. 3, the liposomes prepared from DPPC/chol/PEG-Glu2C$_{18}$ showed no release of calcein at all pH values tested. Likewise, the liposomes of Phytopresome composition used as a control also showed no pH-induced change in their release behavior. However, about 40% calcein release was observed at all pH values tested, indicating that the membrane of the control liposomes was low in encapsulation stability.

In contrast, in the liposomes prepared from DPPC/Lys-Glu2C$_{16}$/PA/chol/PEG-Glu2C$_{18}$ or DPPC/Lys-Glu2C$_{16}$/CHEMS/PEG-Glu2C$_{18}$, the release rate of calcein was less than 10% at pH 6.5, whereas calcein release was enhanced with increase in pH. In the case of DPPC/Lys-Glu2C$_{16}$/PA/chol/PEG-Glu2C$_{18}$, the release rate of calcein was about 10% at pH 7.0, about 35% at pH 8.0, and 60% at pH 9.0. Likewise, in the liposomes prepared from DPPC/Lys-Glu2C$_{16}$/CHEMS/PEG-Glu2C$_{18}$, the release rate of calcein was 20% at pH 7.0, about 40% at pH 8.0, and 60% at pH 9.0. Since the particle size of these liposomes remained unchanged against pH changes, the liposomes would enhance their membrane permeability in response to changes in their zeta potential to thereby facilitate calcein release. Moreover, since calcein release did not occur in the liposomes prepared from DPPC/cholesterol/PEG-Glu2C$_{18}$, it was indicated that a specific behavior was required for release of the encapsulated calcein, in which the zeta potential changes from positive to negative to cause a change in the filled state of lipid molecules constituting a bimolecular membrane.

[7] Time-Dependent Release Behavior of Calcein

Next, the release velocity of calcein was evaluated at pH 6.5, pH 7.5 or pH 8.0. The calcein-encapsulating liposomes prepared above ([lipid]=1 mg/mL, 30 µL each) were each added to 570 µL of 20 mM Tris-buffer (pH 6.5, 7.5 or 8.5) and mixed at 37° C. The release rate at each pH after a given period of time was calculated by the following equation. The results obtained are shown in FIG. 4.

$$\text{Release rate of calcein}(\%) = (I_x - I_0)/(I_T \times 1.1 - I_0) \quad \text{[Equation 3]}$$

Figure 4:
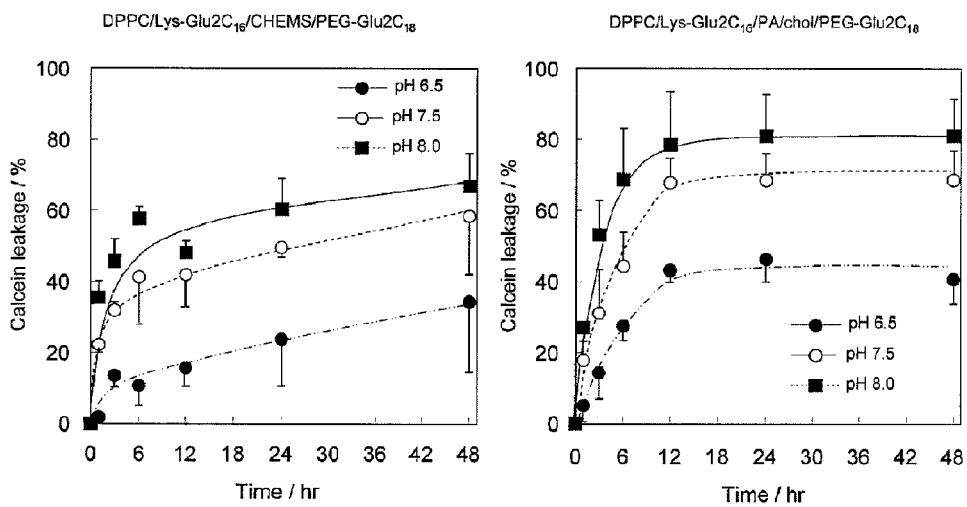
FIG. 4 is graphs showing the time-dependent release behavior of calcein from the calcein-encapsulating liposomes obtained in the Example section.

$I_0$: fluorescence intensity at t=0 (hr)
$I_x$: fluorescence intensity at t=x (hr)
$I_T$: fluorescence intensity upon addition of 200 µL 1% Triton-X As shown in FIG. 4, the liposomes prepared from DPPC/Lys-Glu2C$_{16}$/CHEMS/PEG-Glu2C$_{18}$ showed a release rate of about 30% at pH 6.5, about 55% at pH 7.5, and 65% at pH 8.5 after 48 hours.

In contrast, the liposomes prepared from DPPC/Lys-Glu2C$_{16}$/PA/chol/PEG-Glu2C$_{18}$ showed a release rate of about 40% at pH 6.5, about 65% at pH 7.5, and 80% at pH 8.5 after 48 hours, indicating that the release velocity was higher at each pH than in the liposomes prepared from DPPC/Lys-Glu2C$_{16}$/CHEMS/PEG-Glu2C$_{18}$. This would be because palmitic acid (PA), which is a single chain lipid, results in a poor molecular filling in a bimolecular membrane and hence a high membrane permeability.

[8] Preparation of Citric Acid-Loaded Liposomes

Each lipid mixture (20 mg) was hydrated in 20 mM citric acid (pH 2.2), and the dispersion was subjected to extrusion (final pore size: 0.22 µm) to prepare liposomes having a particle size of 200 to 300 nm. When required, pH change behavior was measured with a pH meter immediately after addition of the liposome dispersion ([lipid]=55 mg/mL, 10 µL) or citric acid (20 mM, 10 µL) to 4 mL of 300 µM aqueous sodium hydroxide (pH 10.5). The results obtained are shown in FIG. 5.

Figure 5:
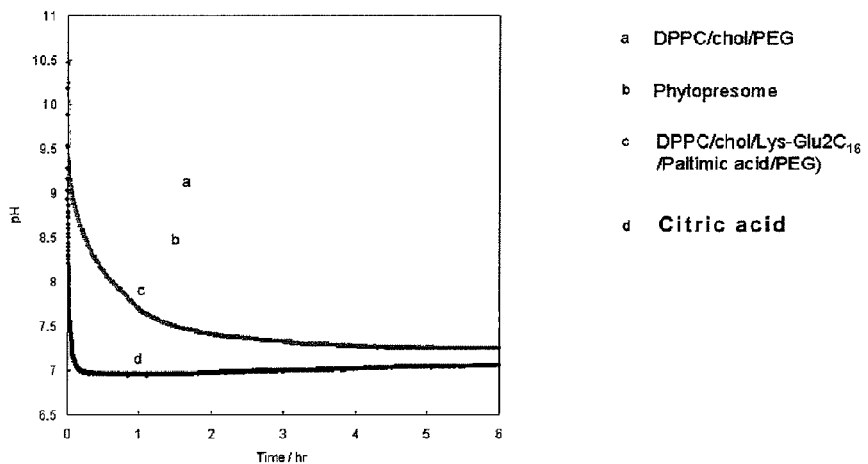
FIG. 5 is a graph showing pH change behavior in the citric acid-loaded liposomes obtained in the Example section.

As shown in FIG. 5, upon addition of citric acid to aqueous sodium hydroxide, the pH was suddenly decreased to 7.0. This pH change would be caused by neutralization reaction between citric acid and sodium hydroxide. Next, upon addition of the DPPC/chol/PEG-Glu2C$_{18}$ liposome dispersion, the pH was gradually decreased and reached pH 7.7 after 6 hours. Phytopresome also showed similar pH changes, although the pH decrease immediately after dropwise addition was faster than in DPPC/cholesterol/PEG-Glu2C$_{18}$. The pH was suddenly decreased upon addition of citric acid alone, whereas the pH was gradually decreased in the liposome dispersion systems. This would be because citric acid within the liposomes is leaked in response to a pH change-induced proton gradient between inner and outer aqueous phases, and the leaked citric acid causes a decrease in pH, thus leading to slower pH changes.

Next, upon addition of the liposomes prepared from DPPC/Lys-Glu2C$_{16}$/PA/chol/PEG-Glu2C$_{18}$, the pH was decreased to 7.5 after 6 hours. This would be because the liposomes release citric acid in response to a weakly basic environment in the outer aqueous phase to thereby cause a more rapid decrease in pH than in the DPPC/cholesterol/PEG-Glu2C$_{18}$ or Phytopresome liposomes. These results indicated a pH change-induced release behavior of the encapsulated citric acid from liposomes. Moreover, it was also suggested that the DPPC/Lys-Glu2C$_{16}$/PA/chol/PEG-Glu2C$_{18}$ liposomes are more likely to release the citric acid encapsulated therein in a weakly basic environment.

[9] Release Behavior of Citric Acid from Liposomes in a Weakly Basic Environment The release behavior of citric acid from liposomes was studied in a weakly basic environment. First, to an aqueous liquid of citric acid having liposomes dispersed therein ([lipid]=250 µM, 4 mL) or an aqueous solution of citric acid (30 mM, pH 2.2, 4 mL), 2M aqueous sodium hydroxide (170 µL) was added to adjust the pH of the mixture to 6.5. Then, 300 mM aqueous sodium hydroxide (60 µL) was added to change the pH of the mixture to 7.5 to 8.5. The subsequent pH change behavior was monitored over time with a pH meter. The results obtained are shown in FIG. 6.

Figure 6:
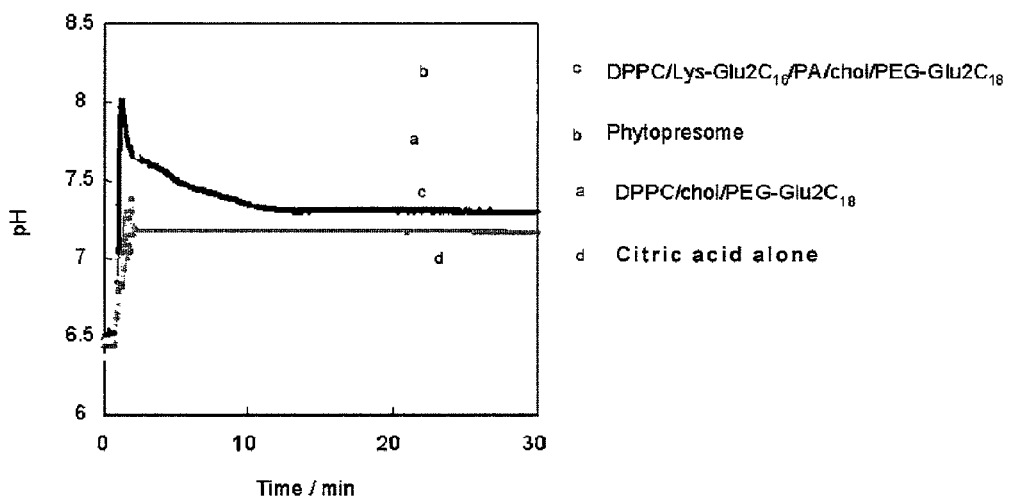
FIG. 6 is a graph showing the release behavior of citric acid in a weakly basic environment from the citric acid-loaded liposomes obtained in the Example section.

As shown in FIG. 6, in the case of citric acid alone, the pH was suddenly decreased and reached a nearly constant value of pH 7. Next, in the case of control liposomes, i.e., DPPC/cholesterol/PEG-Glu2C$_{18}$ and Phytopresome, there was little change in pH even when the pH of the mixture was adjusted from 6.5 to 8. This result indicated that there was little release of the encapsulated citric acid (30 mM, pH 2.2) within 30 minutes.

In contrast, in the case of pH-responsive DPPC/Lys-Glu2C$_{16}$/PA/chol/PEG-Glu2C$_{18}$ liposomes, the pH of the mixture was decreased when the pH reached 8.0. This would be because the encapsulated citric acid was released from the inner aqueous phase of the liposomes in response to pH changes, whereby the pH of the dispersion was controlled.

The above results indicated that when the cationic lipid Lys-Glu2C16 and the anionic lipid PA or CHEMS were used as liposome membrane components, the resulting liposomes changed their zeta potential from positive to negative upon an increase in the pH of the liposome dispersion medium, and thereby enhanced their membrane permeability while retaining their dispersion state. According to the present invention, when a substance such as a fluorescent substance or citric acid is encapsulated in the inner aqueous phase, the encapsulated substance can be released in a weakly basic environment.

INDUSTRIAL APPLICABILITY

The pH-responsive liposomes of the present invention are useful as carriers for drugs, probes, nucleic acids or proteins, etc., and have a pH-responsive behavior never before possible. Thus, pH-responsive formulations can be expected to have a wider range of possibilities.

The invention claimed is:

1. A pH-responsive liposome comprising as a constituent lipid thereof, at least one of the cationic amphiphilic molecules represented by the following formulae:

[Formula 12]

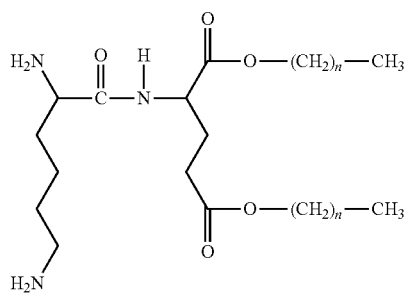

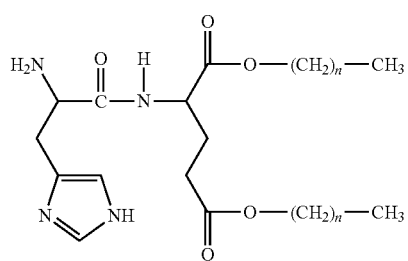

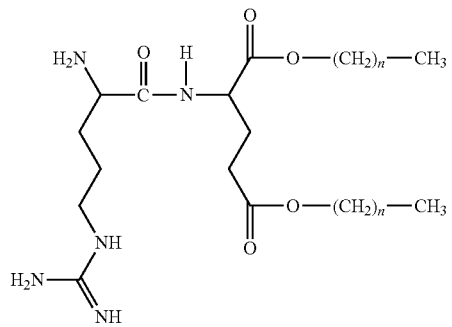

-continued

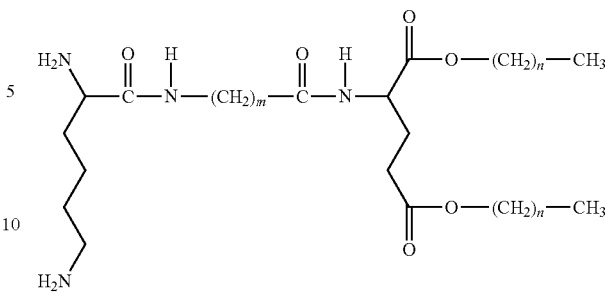

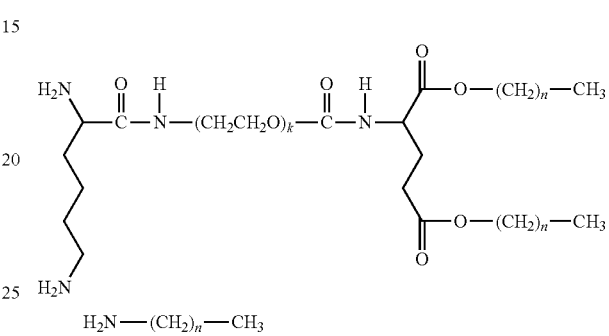

$H_2N-(CH_2)_n-CH_3$ wherein each n is independently an integer of 8 to 22, and m and k are each independently an integer of 1 to 14, and comprising as a constituent lipid thereof at least one of an anionic amphiphilic molecule and a twitterionic amphiphilic molecule represented by the following formulae:

[Formula 13]

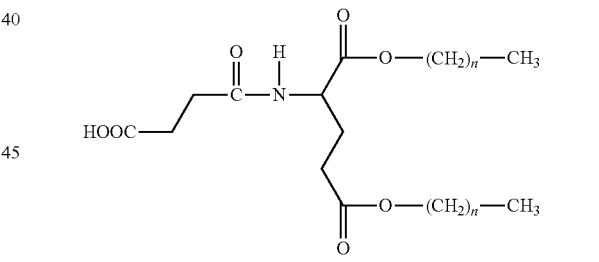

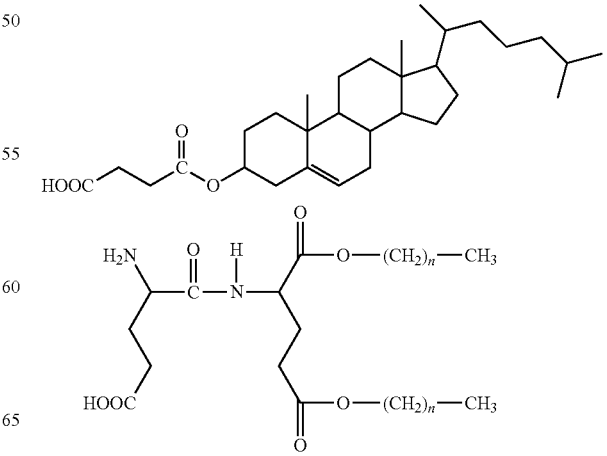

-continued

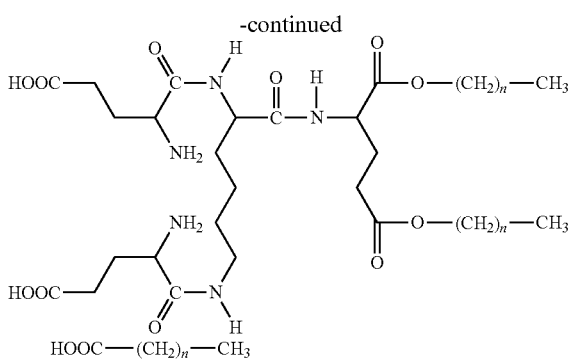

wherein each n is independently an integer of 8 to 22,
wherein the liposome, when dispersed in an aqueous medium, has a positive zeta potential in an acidic environment where the dispersion has a pH of less than 6.5, and has a negative zeta potential in a basic environment where the dispersion has a pH of 8.5 or more.

2. The pH-responsive liposome according to claim 1, which holds a desired substance in an acidic environment where the dispersion has a pH of less than 6.5, and releases the desired substance in a basic environment where the dispersion has a pH of 8.5 or more.

3. The pH-responsive liposome according to claim 1 or 2, which comprises the cationic amphiphilic molecule in an amount of 5 to 95 mol % relative to the total number of moles of constituent lipids in the liposome, and comprises the anionic amphiphilic molecule and/or the twitterionic amphiphilic molecule in a total amount of 5 to 95 mol % relative to the total number of moles of constituent lipids in the liposome.

4. The pH-responsive liposome according to claim 1, wherein the zeta potential of the pH-responsive liposome changes from positive to negative with increase in the pH of the dispersion within a range of pH 7.0 or more to less than pH 8.0.

5. The pH-responsive liposome according to claim 1, which releases the desired substance held therein when the zeta potential changes from positive to negative.

6. The pH-responsive liposome according to claim 1, wherein the cationic amphiphilic molecule comprises a cationic functional group which is easy to ionize in an acidic environment where the dispersion has a pH of less than 6.5 and is difficult to ionize in a basic environment where the dispersion has a pH of 8.5 or more.

7. The pH-responsive liposome according to claim 6, wherein the cationic functional group is selected from the group consisting of an amino group, a guanidino group, an imidazole group and derivatives thereof.

8. The pH-responsive liposome according to claim 1, further comprising a cholesterol molecule in an amount of 0.01 to 30 mol % relative to the total number of moles of constituent lipids in the liposome.

9. The pH-responsive liposome according to claim 1, further comprising a polyethylene glycol-linked amphiphilic molecule in an amount of 0.1 to 50 mol % relative to the total number of moles of constituent lipids in the liposome.

* * * * *